US00PP15922P3

(12) United States Plant Patent
Strope

(10) Patent No.: US PP15,922 P3
(45) Date of Patent: Aug. 16, 2005

(54) **NEW GUINEA *IMPATIENS* PLANT NAMED 'BALCEBPIEL'**

(50) Latin Name: *Impatiens×hawkeri*
Varietal Denomination: Balcebpiel

(75) Inventor: Kerry Strope, Jefferson City, MO (US)

(73) Assignee: Ball Horticultural Company, West Chicago, IL (US)

( * ) Notice: Subject to any disclaimer, the term of this patent is extended or adjusted under 35 U.S.C. 154(b) by 90 days.

(21) Appl. No.: 10/736,736

(22) Filed: Dec. 16, 2003

(65) Prior Publication Data

US 2005/0132455 P1 Jun. 16, 2005

(51) Int. Cl.[7] ..... A01H 5/00
(52) U.S. Cl. ..... Plt./318
(58) Field of Search ..... Plt./318

(56) References Cited

U.S. PATENT DOCUMENTS

PP11,415 P * 6/2000 Trees ..... Plt./318
PP13,698 P2 * 4/2003 Hofmann ..... Plt./318
PP14,864 P2 * 6/2004 Hofmann ..... Plt./318
PP15,223 P2 * 10/2004 Jorna ..... Plt./318

OTHER PUBLICATIONS

UPOV ROM GTITM Computer Database, GTI Jouve Retrieval Software 2004/04 Citations for Balcebpie.*

* cited by examiner

*Primary Examiner*—Kent Bell
*Assistant Examiner*—W. C. Haas
(74) *Attorney, Agent, or Firm*—Wood, Phillips, Katz, Clark & Mortimer

(57) ABSTRACT

A new and distinct cultivar of New Guinea *Impatiens* plant named 'Balcebpiel' characterized by its large pink-colored flowers, medium green-colored foliage, medium upright, mounded growth habit, and excellent basal branching.

1 Drawing Sheet

Latin name of genius and species of plant claimed: *Impatiens hawkeri.*
Variety denomination: 'Balcebpiel'.

BACKGROUND OF THE INVENTION

The present invention relates to a new and distinct New Guinea *Impatiens* plant botanically known as *Impatiens hawkeri* and hereinafter referred to by the cultivar name 'Balcebpiel'.

The new cultivar was developed by the inventor in a controlled breeding program during June 2000 at Arroyo Grande, Calif. The objective of the breeding program was to develop New Guinea *Impatiens* cultivars with numerous large flowers, excellent basal branching and upright compact to moderate growth habits.

The female (seed) parent of 'Balcebpiel' was the proprietary *Impatiens hawkeri* selection designated '1585-4' (not patented), characterized by its upright growth habit, light pink-colored flowers and medium green-colored foliage. The male (pollen) parent of 'Balcebpiel' was proprietary *Impatiens hawkeri* selection designated 'BFP-2565' (not patented), characterized by its pink-colored flowers and dark green-colored foliage. 'Balcebpiel' was discovered and selected as a single flowering plant within the progeny of the above stated cross-pollination in January of 2001 at Arroyo Grande, Calif. and was initially designated '3183-2'.

Asexual reproduction of the new cultivar by terminal stem cuttings taken since January 2001 at West Chicago, Ill. has demonstrated that the new cultivar reproduces true to type with all the characteristics, as herein described, firmly fixed and retained through successive generations of such asexual propagation.

SUMMARY OF THE INVENTION

It was repeatedly found that the cultivar of the present invention:

1. Exhibits large round pink-colored flowers,
2. Forms medium green-colored foliage,
3. Exhibits a good basal branching character, and
4. Exhibits a medium, upright mounded growth habit.

Plants of the new cultivar differ from plants of the female parent primarily in flower color and from plants of the male parent primarily in foliage color.

Of the many commercially available New Guinea *Impatiens* cultivars known to the inventor, 'Balcebpiel' is most similar to 'BFP-844' (U.S. Plant Pat. No. 11,415). However, in side-by-side comparisons conducted in West Chicago, Ill., plants of the new cultivar differed from plants of 'BFP-844' in the following characteristics.

1. Plants of the new cultivar have more branches than plants of 'BFP-844',
2. Plants of the new cultivar have shorter branches than plants of 'BFP-844', and
3. Plants of the new cultivar have larger flowers than plants of 'BFP-844'.

BRIEF DESCRIPTION OF THE PHOTOGRAPH

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balcebpiel'. The plants were grown from rooted cuttings for 14 weeks in a greenhouse at West Chicago, Ill.

DETAILED DESCRIPTION

Figure 1:
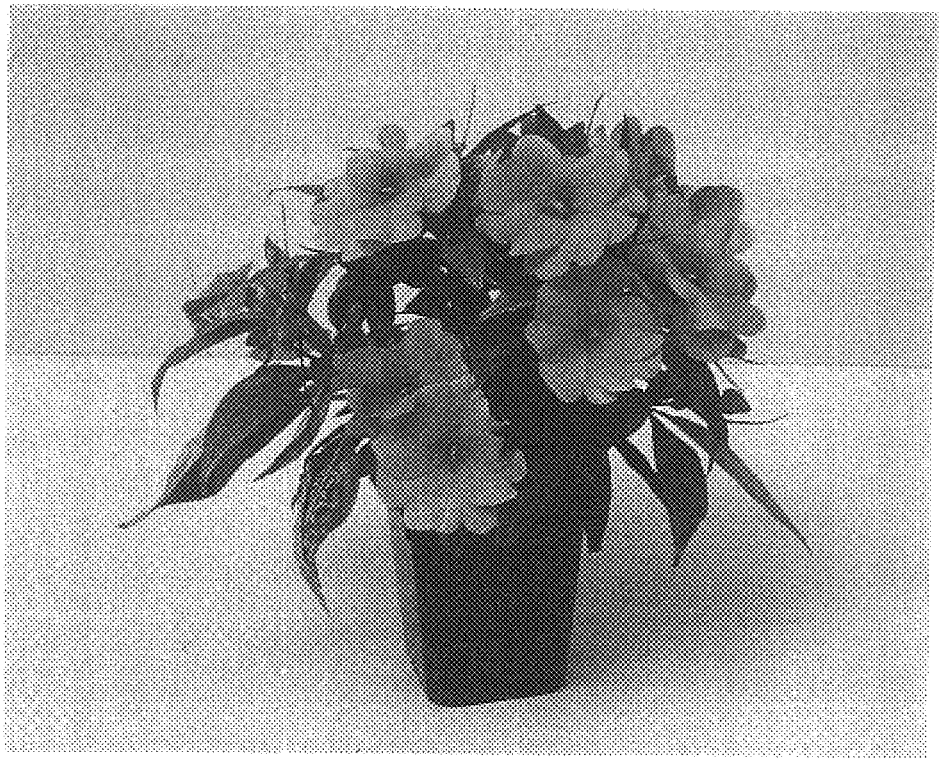
FIG. 1 illustrates a side view of the overall growth and flowering habit of 'Balcebpiel'.
Figure 2:
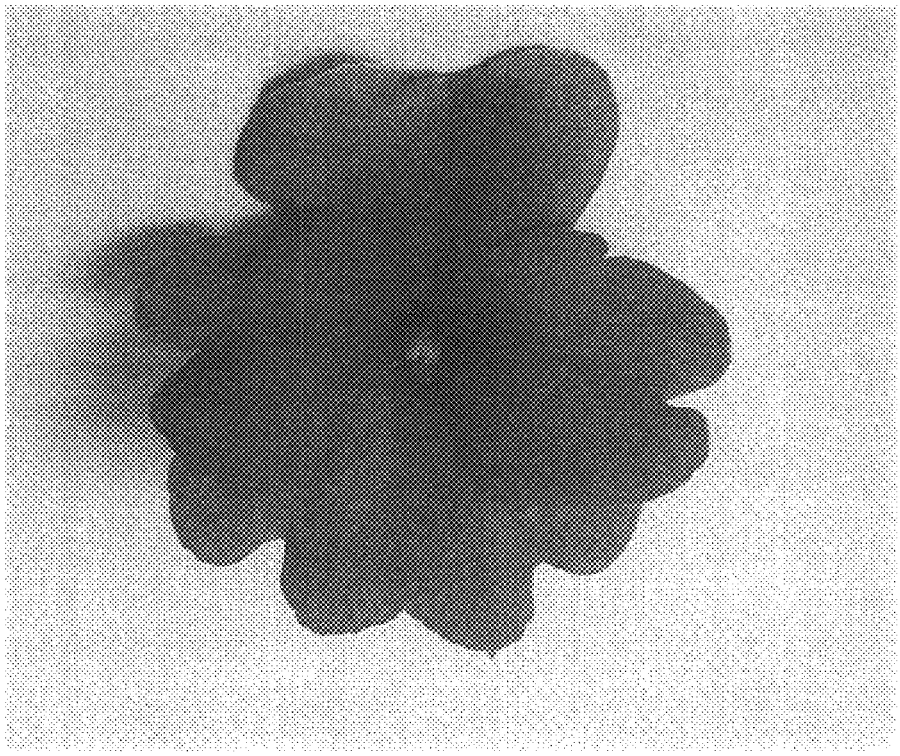
FIG. 2 illustrates a close-up view of a single flower of 'Balcebpiel'.

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 1995 edition, except where general color terms of ordinary significance are used. The color values were determined on Sep. 11, 2003 between 1:00 and 1:45 p.m.under natural daylight conditions.

The following measurements and comparisons describe plants produced from cuttings taken from stock plants and grown under greenhouse conditions comparable to those used in commercial practice. The plants were grown in 10 cm pots for 14 weeks utilizing a soilless growth medium. Greenhouse temperatures were maintained at approximately 72° F. during the day and approximately 65° F. during the night. Greenhouse light levels were maintained at approximately 4,000–7,000 footcandles during the day.

Classification:

*Botanical.*—*Impatiens hawkeri* cultivar 'Balcebpiel'.

Parentage:

*Female* (*seed*) *parent.*—Proprietary *Impatiens hawkeri* selection designated '1585-4' (not patented).

*Male* (*pollen*) *parent.*—Proprietary *Impatiens hawkeri* cultivar 'BFP-2565' (not patented).

Propagation:

*Type cutting.*—Terminal stem.

*Time to initiate roots.*—Approximately 7–14 days.

*Time to develop a rooted cutting.*—Approximately 21 days.

*Root description.*—Fine, fibrous.

*Rooting habit.*—Freely branching.

Plant description:

*Habit of growth.*—Compact with good basal branching. A mature plant, 14 weeks after the planting of a rooted cutting, commonly measures approximately 15 cm from soil level to top of plant plane and approximately 24 cm in width (plant spread).

*Plant form.*—Upright and mounded.

*Branches.*—Quantity per plant: Approximately 2. Length: Approximately 7.4 cm. Diameter: Approximately 9 mm. Texture: Glabrous. Color: 144A. Internode length: Approximately 1.9 cm.

*Foliage.*—Type: Simple. Arrangement of lower leaves: Alternate. Arrangement of upper leaves: Whorls. Shape: Elliptic. Apex: Acuminate. Base: Attenuate. Margin: Serrulate, ciliate. Texture of upper and lower surfaces: Slightly rugose. Pubescence of upper surface: Moderately papillate. Pubescence on lower surface: None. Venation pattern: Pinnate. Size of mature foliage: Length: Approximately 9.7 cm. Width: Approximately 3.7 cm. Color of mature foliage: Upper surface: Slightly darker than 137A, with veins and mid-vein of 145C. Lower surface: 147B with veins and mid-vein of 145B. Petiole: Length: Approximately 1 cm. Diameter: Approximately 3.4 mm. Texture: Upper and lower surfaces: Glabrous. Color: 145B.

Flower description:

*Flower type.*—Single, not fragrant with self-cleaning petals.

*Flowering habit.*—Freely flowering with flowers positioned above the foliage and facing outward or upward.

*Natural flowering season.*—Year round in greenhouse environment. Flowering is continuous from spring until fall in the garden.

*Flower longevity on plant.*—Approximately 10 days.

*Quantity of flowers and buds per stem.*—Approximately 1 fully open flower and 7 buds at any one time.

*Mature flower buds* (*just before opening*).—Shape: Ovoid. Length: Approximately 1.8 cm. Diameter: Approximately 1 cm. Color of petals: Darker than 54A.

*Flower shape.*—Round, flat to slightly cupped.

*Flower size.*—Diameter: Approximately 6.6 cm. Depth: Approximately 1.7 cm.

*Petals.*—Number: Five per flower. Shape: Obovate. Margin: Entire. Apex: Emarginate. Base: Superior petal has truncate base, other four petals have attenuate bases. Texture of upper and lower surfaces: Glabrous. Appearance: Iridescent. Size: Superior petal length: Approximately 2.7 cm. Superior petal width: 4.3 cm. Lateral petal length: 3.2 cm. Lateral petal width: 2.8 cm. Lower petal length: 3.5 cm. Lower petal width: 3.1 cm. Color of upper surface of all petals: 47D with venation of 47B and base darker than N57A. Color of lower surfaces of all petals: 49D with venation of 47B, mid-vein of 59C and base of 47C. Petal color fades with age to 54A.

*Calyx.*—Quantity of sepals: Three, with lower sepal modified into a spur. Sepal shape: Ovate. Sepal apex: Acuminate. Sepal texture of both surfaces: Glabrous. Lateral sepal length: Approximately 1.4 cm. Lateral sepal width: Approximately 6 mm. Lateral sepal color of both surfaces: 145B. Lower sepal length: Approximately 1.5 cm. Lower sepal width: Approximately 7 mm. Lower sepal color of both surfaces: 55D with venation and margin of 55A.

*Spur.*—Quantity: One per flower. Length: Approximately 5.1 cm. Diameter at flower: 3 mm. Diameter at tip: 1 mm. Aspect: Curved downward. Color: 146C overlaid with 59C.

*Peduncles.*—Strength: Strong. Angle to stem: Acute. Length: Approximately 4.6 cm. Diameter: 2 mm. Texture: Glabrous. Color: 145B.

*Reproductive organs.*—Androecium: Five stamens, anthers are fused together forming one organ that surrounds the pistil. Filaments are free. Generally, the anthers shed pollen prior to the stigma becoming receptive. Filament color: 61B. Anther shape: Oval. Anther length: Approximately 3 mm. Anther color: Colorless and translucent. Pollen amount: Moderate. Pollen color: 8D. Gynoecium: Pistil number: One per flower. Pistil length: Approximately 5 mm. Stigma length: 0.5 mm. Stigma color: Colorless and translucent. Style length: 0.5 mm. Style color: 144D and translucent. Ovary length: 4 mm. Ovary diameter: 2 mm. Ovary color: 144A.

Seed and fruit development: Neither seed nor fruit production has been observed.

Disease and pest resistance: Resistance to pathogens and pests common to *Impatiens* has not been observed.

What is claimed is:

1. A new and distinct cultivar of New Guinea *Impatiens* plant named 'Balcebpiel' substantially as herein shown and described, which:

1. Exhibits large round pink-colored flowers,
2. Forms medium green-colored foliage,
3. Exhibits a good basal branching character, and
4. Exhibits a medium upright, mounded grown habit.

* * * * *